US012563643B2

(12) United States Patent
Shavit

(10) Patent No.: US 12,563,643 B2
(45) Date of Patent: Feb. 24, 2026

(54) DRY HEAT THAWING OF BIOLOGICAL SUBSTANCES

(71) Applicant: FreMon Scientific, Inc., La Jolla, CA (US)

(72) Inventor: Menachem Shavit, Demarest, NJ (US)

(73) Assignee: FreMon Scientific, Inc., La Jolla, CA (US)

( * ) Notice: Subject to any disclaimer, the term of this patent is extended or adjusted under 35 U.S.C. 154(b) by 441 days.

(21) Appl. No.: 17/381,943

(22) Filed: Jul. 21, 2021

(65) Prior Publication Data

US 2021/0352768 A1 Nov. 11, 2021

Related U.S. Application Data

(63) Continuation of application No. 15/901,231, filed on Feb. 21, 2018, now abandoned.

(Continued)

(51) Int. Cl.
*H05B 1/02* (2006.01)
*A61J 1/00* (2023.01)
(Continued)

(52) U.S. Cl.
CPC ........... *H05B 1/025* (2013.01); *A61M 1/0281* (2013.01); *H05B 3/02* (2013.01); *A61J 1/00* (2013.01);
(Continued)

(58) Field of Classification Search
None
See application file for complete search history.

(56) References Cited

U.S. PATENT DOCUMENTS

| 2,640,906 A | 6/1953 | Haynes |
| 3,475,590 A | 10/1969 | Pins et al. |
| | (Continued) | |

FOREIGN PATENT DOCUMENTS

| CN | 102802693 A | 11/2012 |
| CN | 105999444 A | 10/2016 |
| | (Continued) | |

OTHER PUBLICATIONS

Corrected Notice of Allowability mailed on Jan. 14, 2020, for U.S. Appl. No. 15/502,642, filed Mar. 7, 2017, 2 pages.

(Continued)

*Primary Examiner* — Elizabeth M Kerr
(74) *Attorney, Agent, or Firm* — Procopio, Cory, Hargreaves & Savitch LLP

(57) ABSTRACT

A device for dry thawing biological substances and methods for using the same are provided. The dry thawing device can be configured to receive a biological substance within a woven pocket. The woven pocket can include temperature sensors configured to measure a temperature of the interior volume and heating elements configured to heat an interior of the woven pocket 106 based upon the measured temperature to avoid overheating or underheating the biological substance during thawing. The woven pocket can also include mechanical vibrators configured to agitate the biological substance during thawing to achieve an approximately homogeneous temperature profile within the woven pocket.

14 Claims, 8 Drawing Sheets

Related U.S. Application Data

(60) Provisional application No. 62/501,314, filed on May 4, 2017.

(51) Int. Cl.
   *A61M 1/02*          (2006.01)
   *H05B 3/02*          (2006.01)

(52) U.S. Cl.
   CPC ... *A61J 2200/42* (2013.01); *A61M 2205/3653* (2013.01); *H05B 2203/002* (2013.01); *H05B 2203/02* (2013.01)

(56)                References Cited

U.S. PATENT DOCUMENTS

| | | | |
|---|---|---|---|
| 3,485,245 A | 12/1969 | Lahr et al. | |
| 3,518,393 A | 6/1970 | Besseling et al. | |
| 3,590,215 A | 6/1971 | Anderson et al. | |
| 3,798,418 A | 3/1974 | Reik et al. | |
| 3,898,023 A | 8/1975 | Faust | |
| 4,309,592 A | 1/1982 | Le Boeuf | |
| 4,486,389 A | 12/1984 | Darnell et al. | |
| 4,535,482 A * | 8/1985 | Spector ............ A41D 19/01535 |
| | | | 2/163 |
| 4,680,445 A | 7/1987 | Ogawa | |
| 4,731,072 A | 3/1988 | Aid | |
| 4,847,470 A | 7/1989 | Bakke | |
| 4,852,641 A | 8/1989 | Noble | |
| 4,967,061 A | 10/1990 | Weber, Jr. et al. | |
| 5,013,889 A | 5/1991 | Bakke | |
| 5,081,697 A | 1/1992 | Manella | |
| 5,114,681 A | 5/1992 | Bertoncini et al. | |
| 5,206,479 A | 4/1993 | Zakaria et al. | |
| 5,245,693 A | 9/1993 | Ford et al. | |
| 5,261,255 A | 11/1993 | Coelho et al. | |
| 5,297,234 A | 3/1994 | Harms et al. | |
| 5,364,385 A | 11/1994 | Harms et al. | |
| 5,368,569 A | 11/1994 | Sanese | |
| H1623 H | 1/1997 | Reed | |
| 5,603,220 A | 2/1997 | Seaman | |
| 5,616,268 A | 4/1997 | Carr | |
| 5,691,452 A | 11/1997 | Gawryl et al. | |
| 5,779,974 A | 7/1998 | Kuzyk | |
| 6,007,773 A | 12/1999 | Kuzyk | |
| 6,142,974 A | 11/2000 | Kistner et al. | |
| 6,159,368 A | 12/2000 | Moring et al. | |
| 6,259,067 B1 | 7/2001 | Faries, Jr. et al. | |
| 6,371,121 B1 | 4/2002 | Faries, Jr. et al. | |
| 6,381,981 B1 | 5/2002 | Yaddgo et al. | |
| 6,384,380 B1 | 5/2002 | Faries, Jr. et al. | |
| 6,419,827 B1 | 7/2002 | Sandell et al. | |
| 6,432,320 B1 | 8/2002 | Bonsignore et al. | |
| 6,452,138 B1 * | 9/2002 | Kochman ................ H05B 3/58 |
| | | | 219/549 |
| 6,503,457 B1 | 1/2003 | Neeper et al. | |
| 6,596,531 B2 | 7/2003 | Campbell et al. | |
| 6,638,761 B2 | 10/2003 | Shin et al. | |
| 6,684,646 B2 | 2/2004 | Voute et al. | |
| 6,698,213 B2 | 3/2004 | Voute et al. | |
| 6,727,480 B2 | 4/2004 | Fernando et al. | |
| 6,730,883 B2 | 5/2004 | Brown et al. | |
| 6,748,164 B1 | 6/2004 | Kuzyk | |
| 6,786,054 B2 | 9/2004 | Voute et al. | |
| 6,824,528 B1 | 11/2004 | Faries, Jr. et al. | |
| 6,861,624 B1 | 3/2005 | Pelster | |
| 6,931,864 B2 | 8/2005 | Fuhr et al. | |
| 6,945,056 B2 | 9/2005 | Brown et al. | |
| 6,996,995 B2 | 2/2006 | Voute et al. | |
| 7,011,797 B2 | 3/2006 | Bakke | |
| 7,019,267 B2 | 3/2006 | Weinfield et al. | |
| 7,041,941 B2 | 5/2006 | Faries, Jr. et al. | |
| 7,077,559 B2 | 7/2006 | Hlavinka et al. | |
| 7,104,074 B2 | 9/2006 | Voute et al. | |
| 7,137,261 B2 | 11/2006 | Brown et al. | |
| 7,228,688 B2 | 6/2007 | Voute et al. | |
| 7,276,675 B2 | 10/2007 | Faries, Jr. et al. | |
| 7,278,278 B2 | 10/2007 | Wowk et al. | |
| 7,307,245 B2 | 12/2007 | Faries, Jr. et al. | |
| 7,353,658 B2 | 4/2008 | Voute et al. | |
| 7,433,030 B2 | 10/2008 | Waldo et al. | |
| 7,452,510 B2 | 11/2008 | Weinfield et al. | |
| 7,603,921 B2 | 10/2009 | Baumfalk et al. | |
| 7,618,808 B1 | 11/2009 | Papp | |
| 7,638,100 B2 | 12/2009 | Dawes | |
| 7,711,251 B2 | 5/2010 | Barkey | |
| 7,722,839 B2 | 5/2010 | Kuzyk | |
| 7,920,802 B2 | 4/2011 | Minagawa | |
| 7,924,169 B2 | 4/2011 | Baumfalk et al. | |
| 7,955,840 B2 | 6/2011 | Belgrader | |
| 7,958,791 B2 | 6/2011 | Zimmermann et al. | |
| 8,012,416 B2 | 9/2011 | Kuzyk | |
| 8,028,532 B2 | 10/2011 | Voute et al. | |
| 8,037,696 B2 | 10/2011 | Shaham et al. | |
| 8,070,354 B2 | 12/2011 | Bungay, III et al. | |
| 8,329,433 B2 | 12/2012 | Belgrader | |
| 8,371,132 B2 | 2/2013 | Cutting et al. | |
| 8,377,030 B2 | 2/2013 | Hyde et al. | |
| 8,448,457 B2 | 5/2013 | Cutting et al. | |
| 8,451,138 B2 | 5/2013 | Zimmermann et al. | |
| 8,539,790 B1 | 9/2013 | Budd | |
| 8,550,703 B2 | 10/2013 | Cutting | |
| 8,852,536 B2 | 10/2014 | Davidowitz et al. | |
| 8,863,532 B2 | 10/2014 | Voute et al. | |
| 8,906,652 B2 | 12/2014 | Belgrader | |
| 8,968,232 B2 | 3/2015 | Kamen et al. | |
| 9,000,332 B2 | 4/2015 | Brown | |
| 9,034,635 B2 | 5/2015 | Termaat et al. | |
| 9,046,292 B2 | 6/2015 | Burke et al. | |
| 9,103,703 B2 | 8/2015 | Baumfalk et al. | |
| 9,121,403 B2 | 9/2015 | Lanigan et al. | |
| 9,140,487 B2 | 9/2015 | Chaffey et al. | |
| 9,173,248 B2 | 10/2015 | Baker | |
| RE45,789 E | 11/2015 | Shei et al. | |
| 9,357,763 B2 | 6/2016 | Cullis et al. | |
| 9,441,893 B2 | 9/2016 | Velayudhan et al. | |
| 9,648,970 B2 | 5/2017 | Lee | |
| 9,707,528 B2 | 7/2017 | Suchocki et al. | |
| 9,764,075 B2 | 9/2017 | Blickhan et al. | |
| 9,833,580 B2 | 12/2017 | Cho | |
| 9,920,970 B2 | 3/2018 | Arnitz et al. | |
| 9,932,632 B2 | 4/2018 | Kreifels et al. | |
| 10,023,833 B2 | 7/2018 | Akerstrom et al. | |
| 10,057,699 B2 | 8/2018 | Maggiore et al. | |
| 10,196,598 B2 | 2/2019 | Baust et al. | |
| 10,202,572 B2 | 2/2019 | Tanaka et al. | |
| 10,208,280 B2 | 2/2019 | Joaquim et al. | |
| 10,221,384 B2 | 3/2019 | Akerstrom et al. | |
| 10,232,331 B2 | 3/2019 | Boettcher et al. | |
| 10,251,389 B2 | 4/2019 | Karnieli et al. | |
| 10,499,458 B2 | 12/2019 | Shavit et al. | |
| 10,576,190 B2 | 3/2020 | Shavit | |
| 10,722,623 B2 | 7/2020 | Shavit | |
| 10,732,083 B2 | 8/2020 | Shavit et al. | |
| 10,816,446 B2 | 10/2020 | Shavit | |
| 10,837,885 B2 | 11/2020 | Shavit et al. | |
| 10,866,173 B2 | 12/2020 | Shavit et al. | |
| 11,448,575 B2 | 9/2022 | Shavit et al. | |
| 2001/0033233 A1 | 10/2001 | Jentsch et al. | |
| 2001/0042743 A1 | 11/2001 | Faries, Jr. et al. | |
| 2003/0082069 A1 | 5/2003 | Kuzyk | |
| 2004/0006999 A1 | 1/2004 | Brown et al. | |
| 2004/0045954 A1 | 3/2004 | Lehman | |
| 2004/0104182 A1 | 6/2004 | Holmes et al. | |
| 2004/0241835 A1 | 12/2004 | Hutmacher et al. | |
| 2004/0265168 A1 | 12/2004 | Bakke | |
| 2005/0126929 A1 | 6/2005 | Mansouri et al. | |
| 2005/0127056 A1 | 6/2005 | Petkov et al. | |
| 2005/0230376 A1 | 10/2005 | Gomez | |
| 2006/0153549 A1 | 7/2006 | Cazzini et al. | |
| 2007/0029311 A1 | 2/2007 | Akashi et al. | |
| 2007/0127901 A1 | 6/2007 | Kuzyk | |
| 2007/0217810 A1 | 9/2007 | Minagawa | |
| 2007/0240432 A1 | 10/2007 | Voute et al. | |
| 2007/0240578 A1 | 10/2007 | DiLeo | |

(56) References Cited

U.S. PATENT DOCUMENTS

| | | |
|---|---|---|
| 2007/0275435 A1 | 11/2007 | Kim et al. |
| 2008/0058694 A1 | 3/2008 | Huang et al. |
| 2008/0310768 A1 | 12/2008 | Hobson et al. |
| 2009/0009290 A1 | 1/2009 | Kneip et al. |
| 2009/0026907 A1 | 1/2009 | Davidowitz et al. |
| 2009/0158755 A1 | 6/2009 | Cutting et al. |
| 2010/0072216 A1 | 3/2010 | Voute et al. |
| 2010/0075405 A1 | 3/2010 | Broadley et al. |
| 2010/0078422 A1 | 4/2010 | Staab |
| 2010/0175393 A1 | 7/2010 | Burke et al. |
| 2010/0206862 A1 | 8/2010 | Defranco et al. |
| 2010/0291536 A1 | 11/2010 | Viljoen et al. |
| 2011/0082437 A1 | 4/2011 | Stacey et al. |
| 2011/0127273 A1 | 6/2011 | Deane et al. |
| 2011/0151482 A1 | 6/2011 | Emery et al. |
| 2011/0186517 A1 | 8/2011 | Hedmann et al. |
| 2011/0198255 A1 | 8/2011 | Baumfalk et al. |
| 2012/0063973 A1 | 3/2012 | Ang et al. |
| 2012/0234817 A1 | 9/2012 | Baker |
| 2012/0330234 A1 | 12/2012 | Balluff et al. |
| 2013/0091890 A1 | 4/2013 | Schryver et al. |
| 2013/0188888 A1 | 7/2013 | Liu et al. |
| 2013/0195804 A1 | 8/2013 | Borody |
| 2013/0304006 A1 | 11/2013 | Toth |
| 2014/0030677 A1* | 1/2014 | Brown ..................... A61C 5/55 433/224 |
| 2014/0071216 A1 | 3/2014 | Hu et al. |
| 2014/0231406 A1 | 8/2014 | Tsang et al. |
| 2014/0262861 A1 | 9/2014 | Crowe et al. |
| 2015/0324760 A1 | 11/2015 | Borowski et al. |
| 2015/0334774 A1* | 11/2015 | Schryver ................. G01K 3/10 219/442 |
| 2016/0010871 A1 | 1/2016 | Baker |
| 2016/0095165 A1 | 3/2016 | Smith, III |
| 2016/0097583 A1 | 4/2016 | Baust et al. |
| 2016/0106624 A1 | 4/2016 | Camisani et al. |
| 2016/0220748 A1 | 8/2016 | Pouchoulin |
| 2016/0243000 A1 | 8/2016 | Gray |
| 2017/0036181 A1 | 2/2017 | Boettcher et al. |
| 2017/0081106 A1 | 3/2017 | Crowe et al. |
| 2017/0135902 A1 | 5/2017 | Scully, Jr. |
| 2017/0257908 A1 | 9/2017 | Schryver et al. |
| 2017/0277829 A1 | 9/2017 | Weggler et al. |
| 2018/0050856 A1 | 2/2018 | Baud et al. |
| 2018/0125754 A1 | 5/2018 | Sanchez et al. |
| 2018/0126345 A1 | 5/2018 | Topp-Manske |
| 2018/0127703 A1 | 5/2018 | Jarvius et al. |
| 2018/0147306 A1 | 5/2018 | Crawley et al. |
| 2018/0163164 A1 | 6/2018 | Husemann et al. |
| 2018/0177180 A1 | 6/2018 | Chapman et al. |
| 2018/0245031 A1 | 8/2018 | Sato et al. |
| 2018/0250666 A1 | 9/2018 | Paul et al. |
| 2018/0251715 A1 | 9/2018 | Paul et al. |
| 2018/0255766 A1 | 9/2018 | Dick et al. |
| 2018/0320126 A1 | 11/2018 | Doody |
| 2018/0324900 A1 | 11/2018 | Shavit |
| 2018/0360023 A1 | 12/2018 | McPherson et al. |
| 2019/0003939 A1* | 1/2019 | Milne ..................... G01N 1/44 |
| 2019/0041308 A1 | 2/2019 | Schryver et al. |
| 2019/0048303 A1 | 2/2019 | Maggiore |
| 2019/0075786 A1 | 3/2019 | Milne et al. |
| 2019/0144811 A1 | 5/2019 | Heese et al. |
| 2019/0152676 A1 | 5/2019 | Murphy |
| 2019/0194593 A1 | 6/2019 | Ozaki et al. |
| 2019/0329248 A1 | 10/2019 | Scherrer et al. |
| 2021/0146026 A1 | 5/2021 | Shavit |
| 2021/0148799 A1 | 5/2021 | Shavit |

FOREIGN PATENT DOCUMENTS

| | | | |
|---|---|---|---|
| DE | 3121280 A1 | 1/1983 | |
| DE | 3225695 A1 | 1/1984 | |
| DE | 3311591 A1 | 10/1984 | |
| DE | 3321603 A1 | 12/1984 | |
| DE | 3500614 A1 | 7/1986 | |
| DE | 3640114 A1 | 6/1988 | |
| DE | 3705596 A1 | 9/1988 | |
| DE | 3723861 A1 | 1/1989 | |
| DE | 3741051 C1 | 6/1989 | |
| DE | 3800283 A1 | 7/1989 | |
| DE | 3900101 A1 | 7/1990 | |
| DE | 4316163 C2 | 4/1995 | |
| DE | 4328321 C2 | 6/1995 | |
| DE | 19503350 C1 | 7/1996 | |
| DE | 4444180 C2 | 4/1997 | |
| DE | 19841556 C1 | 3/2000 | |
| DE | 19940715 C2 | 12/2001 | |
| DE | 10035297 A1 | 2/2002 | |
| DE | 10112465 C1 | 7/2002 | |
| DE | 10238492 A1 | 4/2004 | |
| DE | 10324116 A1 | 1/2005 | |
| DE | 202004017612 U1 | 1/2005 | |
| DE | 10332781 A1 | 2/2005 | |
| DE | 102005036369 A1 | 2/2007 | |
| DE | 202005021496 U1 | 5/2008 | |
| DE | 102007056169 A1 | 5/2009 | |
| DE | 102009011707 A1 | 6/2010 | |
| DE | 102010002895 A1 | 9/2011 | |
| DE | 102010020374 A1 | 11/2011 | |
| DE | 202013101214 U1 | 4/2013 | |
| DE | 202013102927 U1 | 8/2013 | |
| DE | 112015000765 A5 | 11/2016 | |
| DE | 102015113325 A1 | 2/2017 | |
| EP | 0432591 A1 | 6/1991 | |
| EP | 0318924 B1 | 3/1992 | |
| EP | 0396729 B1 | 8/1994 | |
| EP | 0653215 A1 | 5/1995 | |
| EP | 0527944 B1 | 4/1996 | |
| EP | 0786981 B1 | 9/1998 | |
| EP | 1138304 A2 | 10/2001 | |
| EP | 1174703 A2 | 1/2002 | |
| EP | 0880663 B1 | 4/2003 | |
| EP | 1426672 A1 | 6/2004 | |
| EP | 1299138 B1 | 10/2005 | |
| EP | 1441585 B1 | 5/2006 | |
| EP | 1441586 B1 | 6/2006 | |
| EP | 1747790 B1 | 9/2007 | |
| EP | 1476013 B1 | 5/2011 | |
| EP | 2389063 B1 | 10/2012 | |
| EP | 2510965 A1 * | 10/2012 | ............ A61M 5/445 |
| EP | 2547386 A2 | 1/2013 | |
| EP | 2839822 A1 | 2/2015 | |
| EP | 2914104 A2 | 9/2015 | |
| EP | 2976637 A1 | 1/2016 | |
| EP | 2442857 B1 | 8/2016 | |
| EP | 3104917 A1 | 12/2016 | |
| EP | 3016558 B1 | 10/2017 | |
| GB | 952521 A | 3/1964 | |
| JP | 5261625 B1 | 8/2013 | |
| RU | 2552822 C1 | 6/2015 | |
| WO | WO-8807384 A1 | 10/1988 | |
| WO | WO-9221254 A1 | 12/1992 | |
| WO | WO-9509597 A1 | 4/1995 | |
| WO | WO-0014463 A1 | 3/2000 | |
| WO | WO-2010031237 A1 | 3/2010 | |
| WO | WO-2010132627 A2 | 11/2010 | |
| WO | WO-2010132627 A3 | 5/2011 | |
| WO | WO-2011113421 A2 | 9/2011 | |
| WO | WO-2011113421 A3 | 5/2012 | |
| WO | WO-2014146641 A1 | 9/2014 | |
| WO | WO-2015000464 A1 | 1/2015 | |
| WO | WO-2015120843 A1 | 8/2015 | |
| WO | WO-2015175819 A1 | 11/2015 | |
| WO | WO-2016023034 A1 * | 2/2016 | ........... A01N 1/0263 |
| WO | WO-2017025789 A4 | 4/2017 | |
| WO | WO-2017153761 A1 | 9/2017 | |
| WO | WO-2018000051 A1 | 1/2018 | |
| WO | WO-2018010999 A1 | 1/2018 | |
| WO | WO-2018025053 A1 | 2/2018 | |

(56) References Cited

FOREIGN PATENT DOCUMENTS

| WO | WO-2018195107 A1 | 10/2018 |
| WO | WO-2018211437 A1 | 11/2018 |

OTHER PUBLICATIONS

Corrected Notice of Allowability mailed on Oct. 23, 2019, for U.S. Appl. No. 16/405,974, filed May 7, 2019, 2 pages.
Extended European Search Report mailed on Apr. 16, 2021, for EP Application No. 18794801.3, filed on Apr. 2, 2018, 17 pages.
Extended European Search Report mailed on Aug. 13, 2018, for EP Application No. 15 829 831.5, filed on Aug. 10, 2015, 8 pages.
Final Office Action mailed on Jun. 24, 2020, for U.S. Appl. No. 15/901,231, filed Feb. 21, 2018, 16 pages.
Final Office Action mailed on May 10, 2022, for U.S. Appl. No. 16/938,096, filed Jul. 24, 2020, 15 pages.
Final Office Action mailed on May 13, 2022, for U.S. Appl. No. 17/015,678, filed Sep. 9, 2020, 11 pages.
Final Office Action mailed on Sep. 19, 2019, for U.S. Appl. No. 16/260,100, filed Jan. 28, 2019, 18 pages.
International Search Report mailed on Jan. 5, 2016, for PCT Application No. PCT/US2015/044513, filed on Aug. 10, 2015, 4 pages.
International Search Report mailed on Jul. 2, 2018, for PCT Application No. PCT/US2018/025650, filed on Apr. 2, 2018, 2 pages.
International Search Report mailed on Oct. 9, 2019, for PCT Application No. PCT/US2019/031215, filed on May 7, 2019, 9 pages.
Non-Final Office Action mailed on Nov. 22, 2022, for U.S. Appl. No. 16/938,096, filed Jul. 24, 2020, 16 pages.
Non-Final Office Action for U.S. Appl. No. 17/015,678 mailed on Nov. 21, 2022, 11 pages.
Non-Final Office Action mailed on Apr. 9, 2020, for U.S. Appl. No. 16/405,960, filed May 7, 2019, 19 pages.
Non-Final Office Action mailed on Dec. 10, 2019, for U.S. Appl. No. 15/901,231, filed Feb. 21, 2018, 21 pages.
Non-Final Office Action mailed on Dec. 11, 2019, for U.S. Appl. No. 16/405,987, filed May 7, 2019, 10 pages.
Non-Final Office Action mailed on Dec. 12, 2019, for U.S. Appl. No. 16/405,994, filed May 7, 2019, 7 pages.
Non-Final Office Action mailed on Jan. 21, 2021, for U.S. Appl. No. 15/901,231, filed Feb. 21, 2018, 17 pages.
Non-Final Office Action mailed on Jul. 19, 2019, for U.S. Appl. No. 16/405,974, filed May 7, 2019, 9 pages.
Non-Final Office Action mailed on Mar. 25, 2020, for U.S. Appl. No. 16/405,966, filed May 7, 2019, 6 pages.
Non-Final Office Action mailed on May 30, 2019, for U.S. Appl. No. 15/502,642, filed Mar. 7, 2017, 23 pages.
Non-Final Office Action mailed on May 31, 2019, for U.S. Appl. No. 16/260,100, filed Jan. 28, 2019, 24 pages.
Non-Final Office Action mailed on Nov. 12, 2019, for U.S. Appl. No. 16/405,966, filed May 7, 2019, 7 pages.
Non-Final Office Action mailed on Nov. 8, 2021, for U.S. Appl. No. 16/944,848, filed Jul. 31, 2020, 8 pages.
Non-Final Office Action mailed on Oct. 21, 2021, for U.S. Appl. No. 16/938,096, filed Jul. 24, 2020, 13 pages.
Non-Final Office Action mailed on Oct. 29, 2021, for U.S. Appl. No. 17/015,678, filed Sep. 9, 2020, 10 pages.
Non-Final Office Action mailed on Sep. 26, 2019, for U.S. Appl. No. 16/405,960, filed May 7, 2019, 23 pages.
Notice of Allowance mailed on Aug. 12, 2020, for U.S. Appl. No. 16/405,960, filed May 7, 2019, 11 pages.
Notice of Allowance mailed on Jul. 6, 2020, for U.S. Appl. No. 16/405,966, filed May 7, 2019, 6 pages.
Notice of Allowance mailed on Jun. 5, 2020, for U.S. Appl. No. 16/405,987, filed May 7, 2019, 9 pages.
Notice of Allowance mailed on Mar. 17, 2020, for U.S. Appl. No. 16/260,100, filed Jan. 28, 2019, 8 pages.
Notice of Allowance mailed on Mar. 23, 2020, for U.S. Appl. No. 16/405,994, filed May 7, 2019, 8 pages.
Notice of Allowance mailed on May 13, 2022, for U.S. Appl. No. 16/944,848, filed Jul. 31, 2020, 9 pages.
Notice of Allowance mailed on Sep. 20, 2019, for U.S. Appl. No. 15/502,642, filed Mar. 7, 2017, 10 pages.
Notice of Allowance mailed on Sep. 3, 2019, for U.S. Appl. No. 16/405,974, filed May 7, 2019, 8 pages.
Written Opinion of the International Searching Authority mailed on Jan. 5, 2016, for PCT Application No. PCT/US2015/044513, filed on Aug. 10, 2015, 13 pages.
Written Opinion of the International Searching Authority mailed on Jul. 2, 2018, for PCT Application No. PCT/US2018/025650, filed on Apr. 2, 2018, 7 pages.
Written Opinion of the International Searching Authority mailed on Oct. 9, 2019, for PCT Application No. PCT/US2019/031215, filed on May 7, 2019, 13 pages.
Office Action for EP App No. 18794801.3 dated Mar. 1, 2024, 5 pgs.
Communication Under Rule 71(3) for EP App No. 18794801.3, dated Jan. 27, 2025, 8 pgs.
Extended European Search Report (EESR) mailed Dec. 3, 2025 for European Application No. 251865873.9, 8 pages.

\* cited by examiner

COMPUTING
DEVICE,
104

102

112

116

114     106

600

Place enclosure containing a frozen biological substance in a dry thawing device, 602

Command heating elements of the dry thawing device to generate heat, 604

Measure temperature of the enclosed biological substance as a function of time, 606

Command the heating elements to adjust the generated heat based upon the measured temperature, 610

DRY HEAT THAWING OF BIOLOGICAL SUBSTANCES

CROSS REFERENCE TO RELATED APPLICATIONS

This application is a continuation of U.S. patent application Ser. No. 15/901,231, filed on Feb. 21, 2018, which claims priority to U.S. Provisional Application No. 62/501,314 filed on May 4, 2017 and entitled "Dry Heat Thawing of Biological Substances," each of which is hereby incorporated by reference in its entirety.

FIELD

Methods and devices are provided for dry thawing biological substances.

BACKGROUND

Bags containing biological substances such as plasma, blood, blood products, and medication can be supplied to medical facilities for transfusion in large volume on a daily basis. These bags can be are frozen, stored into inventory upon arrival, and thawed to a designated temperature before transfusion.

The quality of thawed biological substances can depend upon the process by which they are thawed. Underheating the biological substances can cause patients to experience hypothermia. Conversely, overheating the biological substances can cause severe damage (e.g., denaturation) to proteins and other components and reduce the quality of the transfused fluid, endangering patients. Accordingly, there is a need for improved methods and devices for thawing biological substances.

SUMMARY

In general, systems and methods for dry thawing biological substances are provided.

In one embodiment, a dry thawing device is provided and can include a woven pocket having an inner volume dimensioned to receive a biological substance. The woven pocket can include one or more temperature sensors configured for thermal communication with a biological substance received within the woven pocket. The woven pocket can also include one or more heating elements configured to supply heat to the inner volume based upon temperature measurements acquired by one or more of the temperature sensors.

The woven pocket can have a variety of configurations. In one embodiment, the woven pocket can be formed from one or more electrically conductive fibers interwoven with one or more electrically insulating fibers, where the heating elements can include the electrically conductive fibers. The electrically conductive fibers can be formed from a positive temperature coefficient (PTC) material.

In another embodiment, the woven pocket can be formed from electrically insulating fibers and the heating element can be printed on an outer surface of an enclosure containing the biological substance.

In another embodiment, the woven pocket can be formed from electrically insulating fibers and the heating element can be positioned on an inner surface of the inner volume of the woven pocket.

In another embodiment, the woven pocket can be formed from electrically insulating fibers and the heating element can be woven into an outer surface of the woven pocket.

In another embodiment, the dry thawing device can include one or more mechanical vibrators in mechanical communication with the woven pocket.

In another embodiment, the dry thawing device can include a frame having an aperture formed therein, where the woven pocket is disposed within the aperture and an open end of the woven pocket can be coupled to the frame.

In another embodiment, the dry thawing device can include an electrical interface mounted to the frame and electrically coupled with the heating element and the temperature sensors.

In another embodiment, the dry thawing device can include a liquid-resistant coating lining an inner surface of the woven pocket.

In another embodiment, the dry thawing device can include nn adaptor positioned within the inner volume and having one or more chambers. The the adaptor can be configured to conduct heat generated by the heating elements to a vessel containing a biological substance that is received within a chamber.

In one embodiment, a system for dry thawing a biological substance is provided and can include a dry thawing device and a rigid housing. The dry thawing device can include a woven pocket configured to receive a biological substance and to deliver heat to a biological substance received therein in response to one or more commands received at a first electrical interface of the dry thawing device. The housing can be dimensioned to enclose the dry thawing device therein and include a second electrical interface configured to engage the first electrical interface for delivering the one or more commands to the dry thawing device.

The dry thawing device can have a variety of configurations. In one embodiment, the dry thawing device can include one or more heating elements integrated into the woven pocket for delivering heat to a biological substance received therein in response to the one or more commands. The dry thawing device can include one or more temperature sensors configured to acquire one or more temperature measurements of a biological substance received therein and communicate the acquired temperature measurements to the first electrical interface. The one or more commands can be based upon the acquired temperature measurements.

In another embodiment, the system can include a computing device in communication with the second electrical interface. The computing device can be configured to receive the acquired temperature measurements and generate the one or more commands based upon a difference between the acquired temperature measurements and a predefined temperature set point.

In another embodiment, the dry thawing device can include one or more mechanical vibrators configured to agitate a biological substance received within the woven pocket in response to the one or more commands.

In another embodiment, the dry thawing device can include a rigid frame coupled to the woven pocket, where the first electrical connector can be mounted to the frame. The housing can be configured to support at least a portion of the dry thawing device at the frame.

Methods for dry thawing a biological substance are also provided. In one embodiment, a method can include activating a dry thawing device having biological substance disposed in an inner volume of a woven pocket to cause a heat to be delivered at a first temperature to the biological substance. A temperature sensor can obtain a temperature measurement of the biological substance and cause the woven pocket to deliver heat at a second temperature different from the first temperature to thereby control heating of the biological substance in the woven pocket.

The woven pocket can have a variety of configurations. In one aspect, the woven pocket can be formed from one or more electrically conductive fibers interwoven with one or more electrically insulating fibers. Delivering heat to the biological substance can include resistively heating the electrically conductive fibers. In another aspect, the woven pocket can be formed from electrically insulating fibers and delivering heat to the biological substance can include resistively heating one or more electrically conductive fibers positioned on an outer surface of an enclosure containing the biological substance. In another aspect, the woven pocket can be formed from electrically insulating fibers and delivering heat to the biological substance can include resistively heating one or more electrically conductive fibers positioned on an inner surface of the inner volume of the woven pocket. In certain embodiments, the electrically conductive fibers can be formed from a positive temperature coefficient (PTC) material.

In another embodiment, the method can include vibrating the woven pocket to cause heat delivered to the biological substance to distribute approximately uniformly therein. At least a portion of the vibrations can be generated by one or more mechanical vibrators in mechanical communication with the woven pocket.

In one embodiment, the woven pocket can be disposed within an aperture of a frame and an open end of the woven pocket can be coupled to the frame. The woven pocket can deliver heat to the biological substance in response to signals received via an electrically interface mounted to the frame.

In one embodiment, the method can also include thermally insulating the temperature sensor from the heating element.

BRIEF DESCRIPTION OF THE DRAWINGS

These and other features will be more readily understood from the following detailed description taken in conjunction with the accompanying drawings, in which:

FIG. 1 is a diagram illustrating one exemplary embodiment of a dry thawing system including a computing device and a dry thawing device configured to thaw a biological sub stance;

Figure 2A:
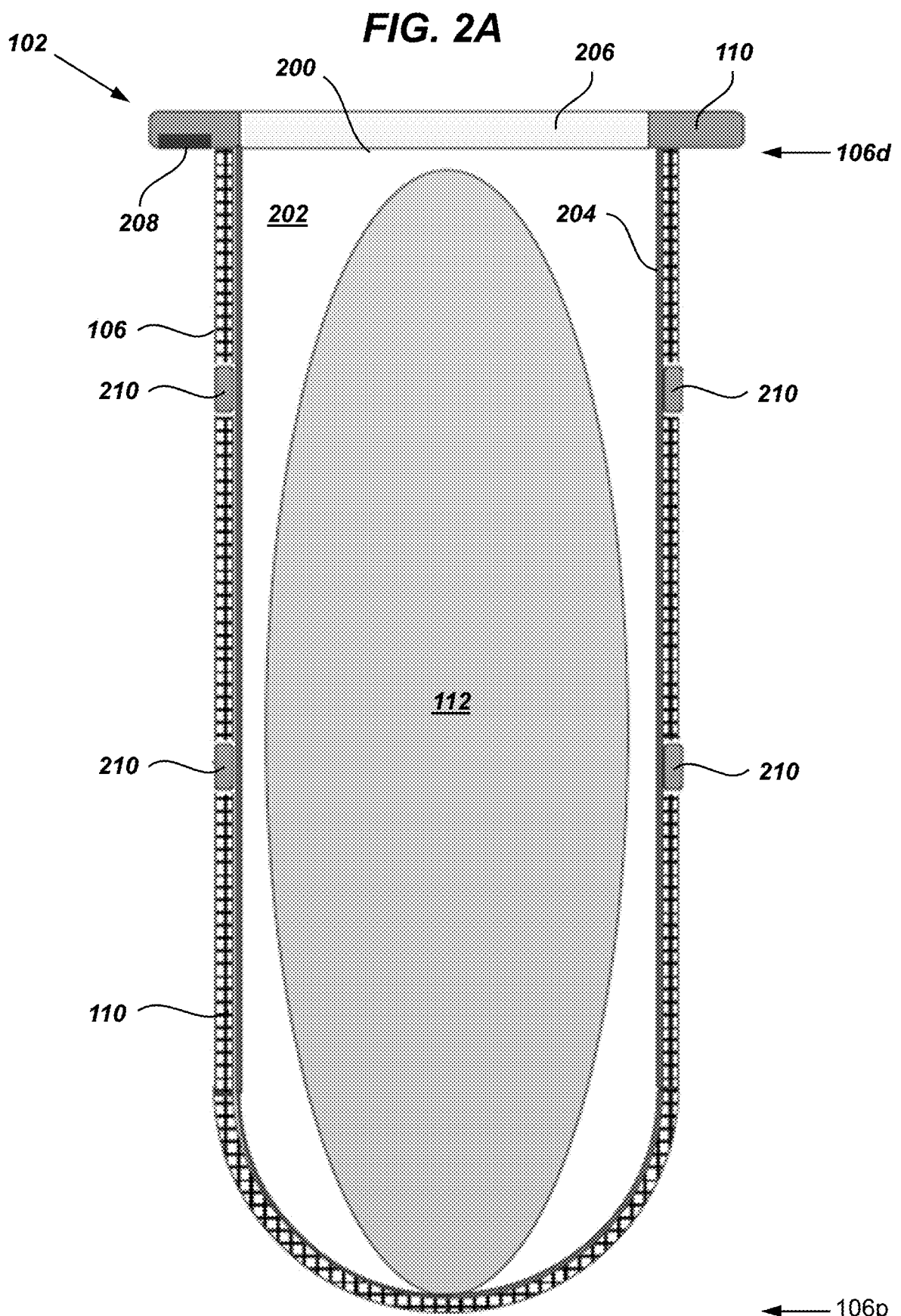
FIG. 2A is a side cross-sectional view of one exemplary embodiment of a dry thawing device including a frame and a woven pocket dimensioned to receive a biological substance.

It is noted that the drawings are not necessarily to scale. The drawings are intended to depict only typical aspects of the subject matter disclosed herein, and therefore should not be considered as limiting the scope of the disclosure.

DETAILED DESCRIPTION

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

Existing systems for thawing bags containing frozen biological substances (e.g., medication, plasma, glycerolized blood, red blood corpuscles (RBCs), etc.) operate by placing frozen bags of biological substances in contact with heated water (e.g., water baths or water bladders). Heat transfer from the water over a selected time duration to ensure that the biological substances are thawed to a desired temperature range. However, these systems do not individually monitor the temperature of each bag for quality control during the thawing process. Typically, the ambient temperature of the water bath or water bladder is monitored during the thawing process. Alternatively, at best, sampled quantities of biological substances are evaluated after thawing. Thus, it can be difficult to achieve reproducible and consistent thawing of the biological substances, creating opportunities for errors that can be harmful to patients. Accordingly, a dry thawing device is provided that can enclose bags containing biological substances and supply heat to an enclosed bag without an intermediate heat conducting fluid (e.g., water baths or water bladders). The applied heat can be dynamically controlled based upon temperature measurements acquired at about a surface of the bag. Temperature measurements can also be recorded to provide a complete temperature record during the thawing process.

Embodiments of the disclosure are discussed herein with respect to thawing biological substances such as medications and blood. Examples of such biological substances can include, but are not limited to, whole blood, blood products, plasma derivatives, etc. However, a person skilled in the art will appreciate that the disclosed embodiments can be employed to thaw any substances without limit.

Figure 1:
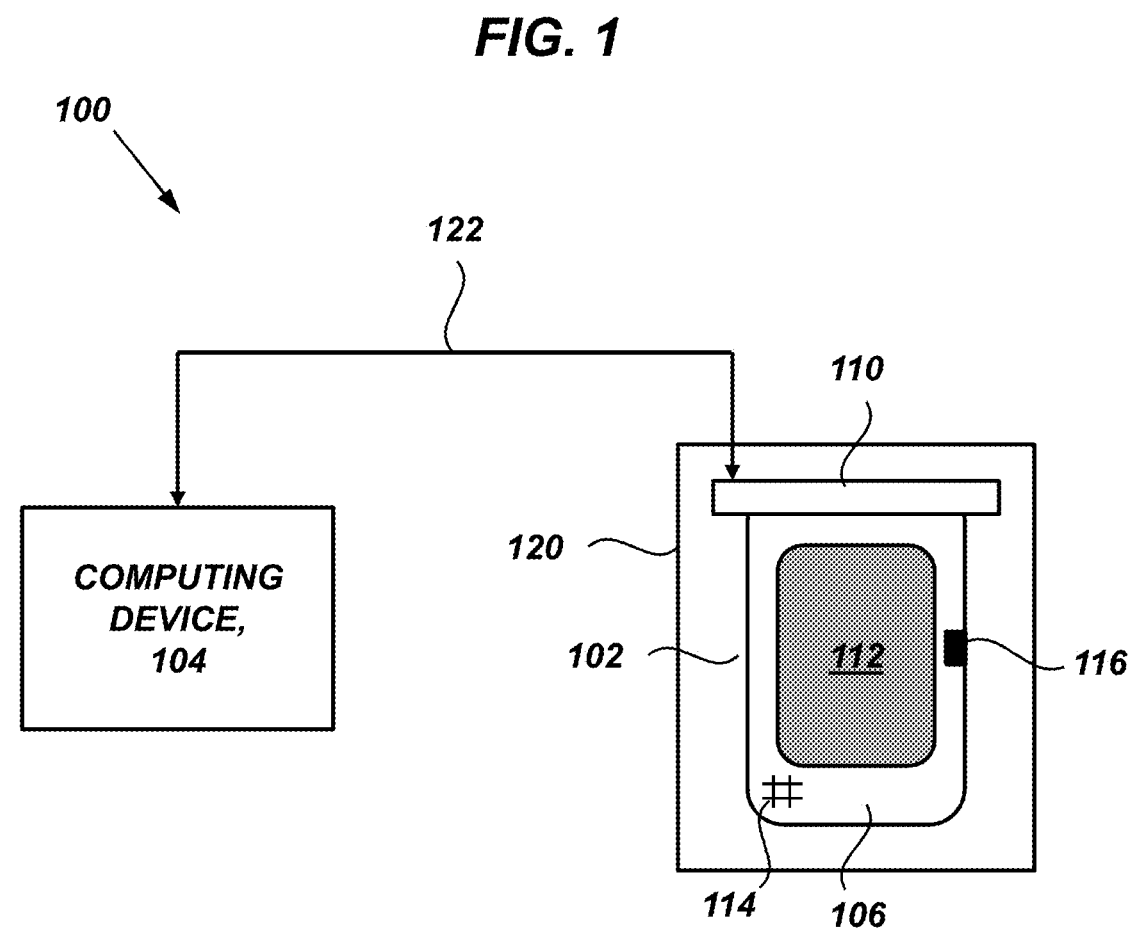

FIG. 1 illustrates one exemplary embodiment of a dry thawing system 100 for thawing biological substances. As discussed in greater detail below, the dry thawing system 100 can include a dry thawing device 102 and a computing device 104. The dry thawing device 102 can include a woven pocket 106 coupled to a frame 110. The woven pocket can be configured to receive and contain a bag 112 or other vessel that contains a biological substance. The woven pocket 106 can also include one more heating elements 114 and one or more temperature sensors 116. In certain embodiments, the dry thawing system 100 can also include a housing 120 configured to receive the dry thawing device 102 therein.

The computing device 104 can be maintained remotely from the housing 120 or integrated with housing 120. When the dry thawing device 102 is positioned within the housing 120, the computing device 104 can be placed in communication with the dry thawing device 102 by a communication link 122. The communication link 122 can be a computing network and can be wired, wireless, or combinations thereof and can allow communication between the computing device 104 and one or more of the heating elements 114 and the temperature sensors 116.

The dry thawing system 100 can be configured to thaw a biological substance disposed within the dry thawing device 102 without the use of water baths or water bladders. In an embodiment, the heating elements 114 can be configured as a portion of the fibers forming the woven pocket 106 and they can supply heat to the biological substance directly or through the bag 112. The temperature sensors 116 can be configured to measure temperatures within the woven pocket 106 (e.g., temperatures of the biological substance) and transmit the measured temperatures to the computing device 104. The computing device 104 can receive and store temperature measurements from the temperature sensors 116 and compare the measured temperatures to pre-defined reference temperatures. The computing device 104 can also transmit commands to the heating elements 114 for controlling an amount of heat supplied to the bag 112 by the heating elements 114 based upon differences between the reference temperatures and the measured temperatures. Thus, regardless of the geometry or volume of the bag 112, heat applied to the bag 112 for thawing a biological substance can be controlled to avoid overheating or underheating the biological substance.

Figure 2B:
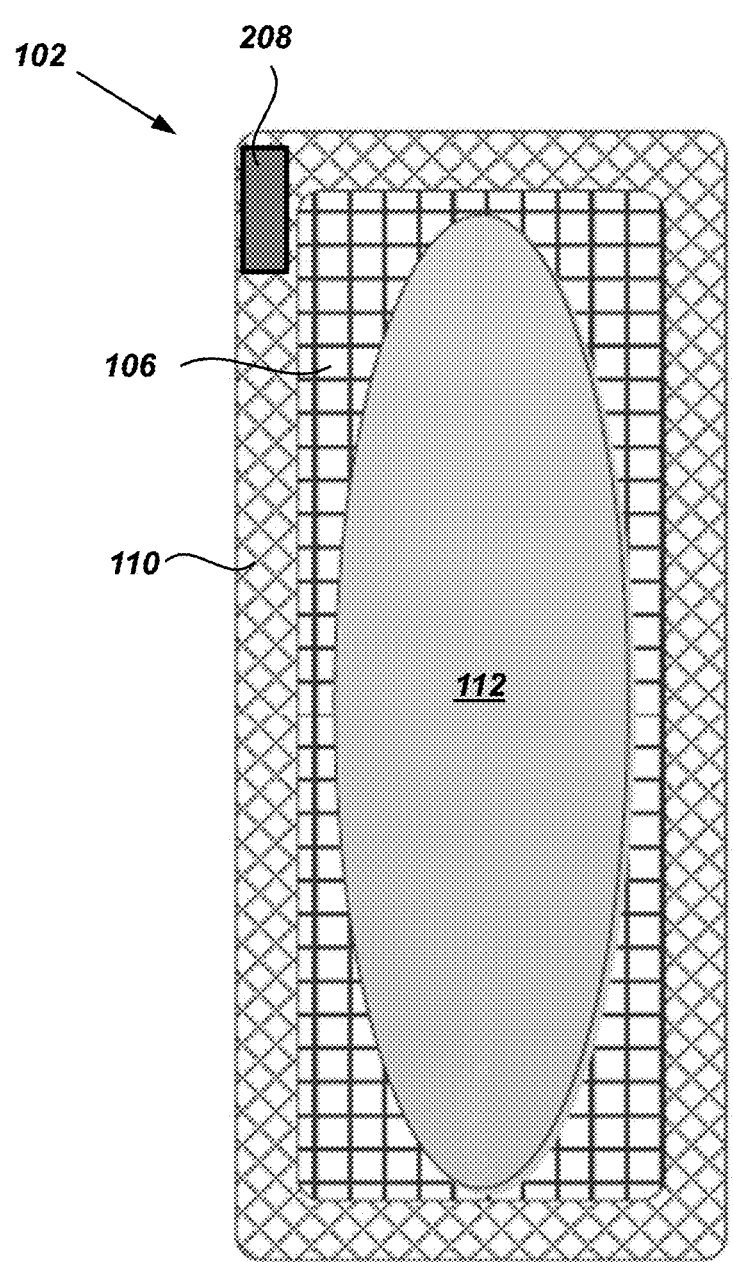
FIG. 2B is a top view of the dry thawing device of FIG. 2A.

FIGS. 2A-2B illustrate one exemplary embodiment of the dry thawing device 102 in greater detail. As shown, the woven pocket 106 can include a sidewall extending between a proximal end 106p and a distal end 106d. An opening 200 can be formed in the distal end 106d of the woven pocket 106 for accessing an inner volume 202 and the proximal end 106p of the woven pocket 106 can be closed. The opening 200 and the inner volume 202 can be dimensioned to receive the bag 112. In certain embodiments, the woven pocket 106 can be formed from one or more woven fibers, as described in greater detail below, providing a generally flexible structure that can accommodate bags 112 having various sizes. As shown, the woven pocket 106 is formed in a generally elongated shape, however, a person skilled in the art will appreciate that the geometry of the woven pocket can be formed in any shape and size necessary to accommodate bags of predetermined size (e.g., about 250 ml to about 500 ml) within the inner volume.

The woven pocket 106 can include a coating 204 lining an inner surface of the inner volume 202. The coating 204 can be formed from a liquid-resistant or liquid-impermeable material, allowing the woven pocket 106 to retain biological substances that may leak from the bag 112 within the inner volume 202. Examples of the coating 204 can include, but are not limited to, silicones.

FIGS. 2A-2B also illustrate the frame 110. The frame 110 can include an aperture 206 formed therethrough and a cover (not shown) configured to reversibly seal the aperture 206. The distal end 106d of the woven pocket 106 can be coupled to the frame 110 such that the inner volume 202 of the woven pocket 106 can be accessed through the opening 200 of the woven pocket 106 and the aperture 206 of the frame 110 when the cover is removed from the aperture 206.

As shown, the frame 110 is formed in a generally planar and rectangular shape. However alternative embodiments of the frame can adopt other shapes (e.g., oval, circular, etc.) and can be planar or non-planar as necessary to accommodate passage of bags through the aperture.

The frame 110 can be formed from a material possess a stiffness greater than the woven pocket 106. Examples of such materials can include, but are not limited to, plastics, metals, and ceramics. The stiffness of the frame 110 can allow it to function as a point of engagement for mounting the dry thawing device 102 to a support structure (e.g., the housing 120) during storage and/or use.

The temperature sensors 116 are also illustrated in FIGS. 2A-2B. In general, the temperature sensors 116 can be provided in any number and positioned at any location suitable for thermal communication with the bag 112 disposed within the woven pocket 106 (e.g., spaced horizontally and/or vertically along the sidewalls of the woven pocket 106). The temperature sensors 116 can be intertwined, woven, threaded, and/or glued into or onto the outer wall of the woven pocket 106 to secure the temperature sensors 116 thereto. As shown, three pairs of temperature sensors 116 are secured to the surface of the inner volume 202 and spaced vertically along the sidewall of the woven pocket 106. In certain embodiments, woven pocket 106 can be dimensioned such that one or more of the temperature sensors 116 can be in thermal communication (e.g., in contact) with an outer surface of the bag 112 when received within the woven pocket 106.

Each of the temperature sensors 116 can be electrically coupled with an electrical interface 208 (e.g., a wiring harness) mounted to the frame 110. As an example, electrical wires (not shown) extending from the temperature sensors 116 can be intertwined, threaded, and/or glued to the outer wall of the woven pocket 106 for routing to the electrical interface 208. The electrical interface 208 can include a printed circuit board (PCB) that has conductive pads for connection to the temperature sensor wires. The conductive pads can be arranged in rows and configured to engage a spring pin connector. As an example, the electrical interface 208 can be configured to engage a corresponding electrical connector mounted to the housing 120 for communication with the computing device 104. Thus, temperature measurements acquired by the temperature sensors 116 to be transmitted to the computing device 104. While illustrated as mounted to the frame 110, alternative embodiments of the electrical interface can be mounted to the bag itself.

Embodiments of the temperature sensors 116 can be any device capable of measuring temperature within a predefined temperature range and of outputting one or more signals representative of the measured temperatures. Examples of temperature sensors 116 can include, but are not limited to, resistance temperature detectors (RTDs) such as thermistors. RTDs can include a sensing element exhibiting an electrical resistance that reproducibly increases or decreases with temperature over a defined operating temperature range. Other embodiments of temperature sensors include wired or wireless radio frequency identification (RFID) temperature sensors.

The woven pocket 106 can also include one or more mechanical vibrators 210 configured to mechanically communicate with the bag 112 when disposed within the woven pocket 106. The mechanical vibrators 210 can be configured to generate low frequency mechanical vibrations (e.g., about 0.1 Hz to about 50 KHz) that facilitate homogenous thawing within the bag 112, as discussed in greater detail below. In certain embodiments, the mechanical vibrators can be piezo-electric vibration devices.

In general, the mechanical vibrators 210 can be provided in any number and positioned at any location suitable for mechanical communication with the bag 112 when disposed within the woven pocket 106. For instance, the mechanical vibrators 210 can be spaced horizontally and/or vertically along the sidewalls of the woven pocket 106). As an example, the mechanical vibrators 210 can be intertwined, threaded, and/or glued to the outer wall of the woven pocket 106 to secure the mechanical vibrators 210 thereto. As shown in FIG. 2A, two pairs of mechanical vibrators 210 are secured to the woven pocket 106, outside of the inner volume 202. Each member of the pair of mechanical vibrators 210 can be positioned on opposing sides of the inner volume 202 and respective pairs of mechanical vibrators 210 can be vertically spaced from one another.

The mechanical vibrators 210 can also be provided in electrical communication with the electrical interface 208 for receipt of command signals from the computing device 104. These command signals can command the mechanical vibrators 210 to start, stop, and/or vary the frequency of mechanical vibrations. As an example, electrical wires (not shown) extending from the mechanical vibrators 210 can be intertwined, threaded, and/or glued to the outer wall of the woven pocket 106 for routing to the conductive pads of the electrical interface 208. Examples of mechanical vibrators 210 can include, but are not limited to, eccentric rotating mass vibration motors (ERMs), linear resonant actuators (LRAs), and combinations thereof.

Figure 3A:
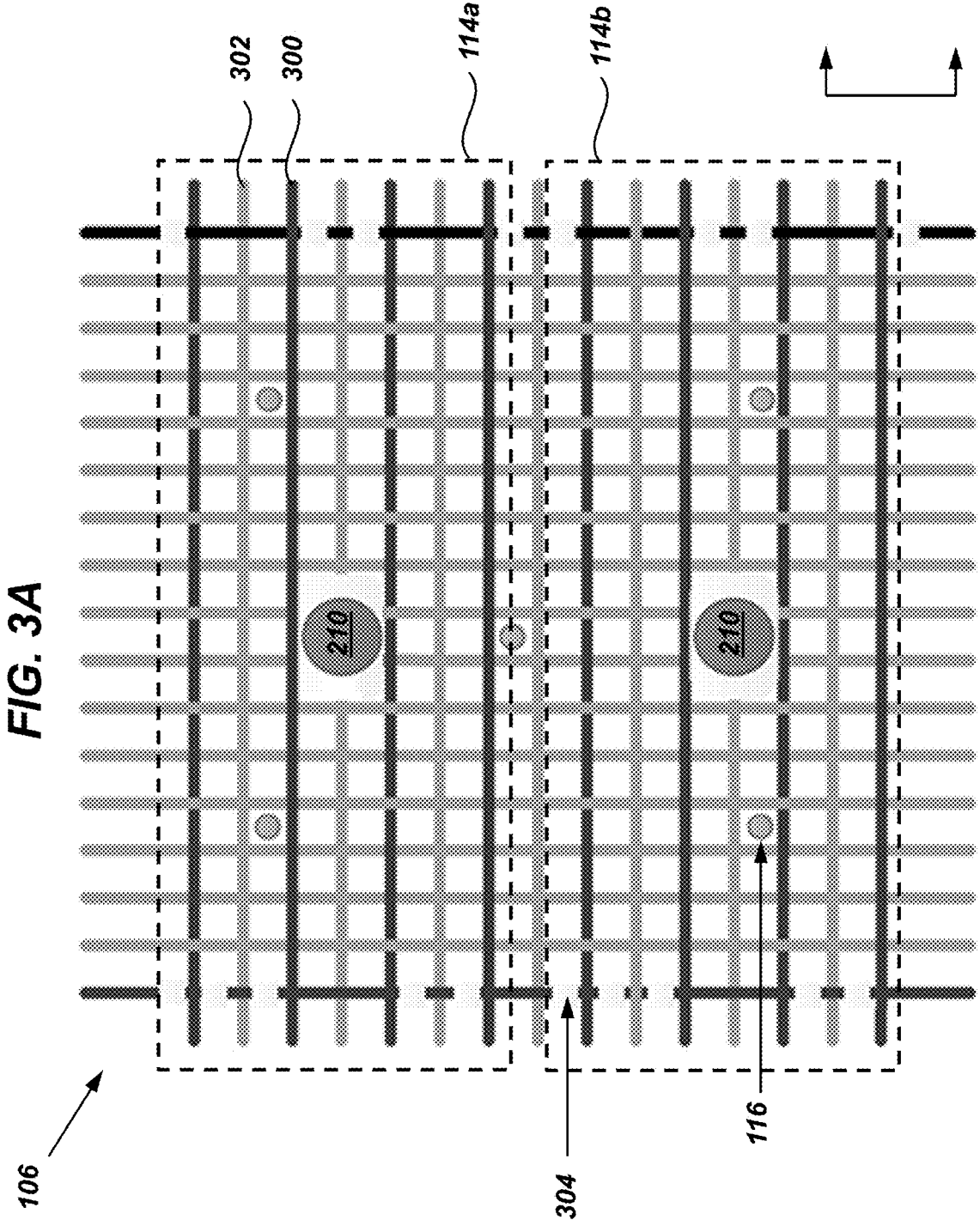
FIG. 3A is an enlarged view of a portion of the woven pocket of the dry thawing device of FIG. 2A including interwoven electrically conductive and non-conductive fibers.
Figure 3B:
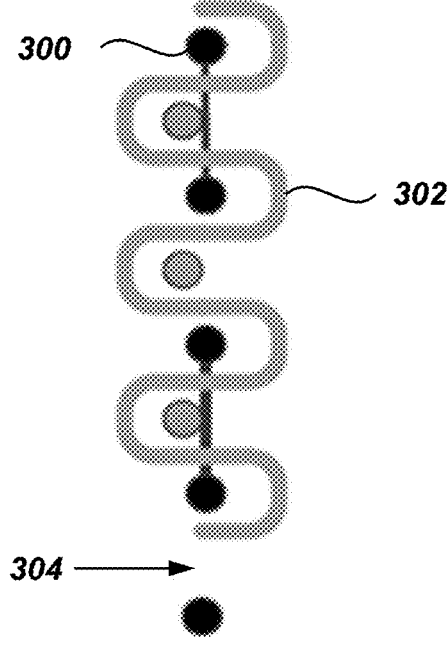
FIG. 3B is a schematic view of a weave of the electrically conductive and non-conductive fibers of FIG. 3A.

FIGS. 3A-3B illustrate the structure of the woven pocket 106 in greater detail. FIG. 3A is an expanded view of a portion of the woven pocket 106 and illustrates that the woven pocket 106 can be formed from a combination of electrically conductive fibers 300 interwoven with electrically insulating fibers 302. The electrically conductive fibers 300 and electrically insulating fibers 302 can be woven in any type of weave. Weaves can include, but are not limited to, plain weaves, harness weaves, satin weaves, twill weaves, etc. As an example, FIG. 3B illustrates an electrically conductive fiber 300 in a plain weave with an electrically insulating fiber 302.

The electrically conductive fibers 300 can be configured to form the heating elements 114. As an example, the electrically conductive fibers 300 can be provided in electrical communication with the electrical interface 208 for receipt of electrical current. Upon receipt of electrical current, the electrically conductive fibers 300 can undergo resistive heating to supply heat to the bag 112 disposed within the woven pocket 106. As discussed in greater detail below, the amount and duration of electrical current supplied to the heating elements 114 can be controlled by the computing device 104.

The heating elements 114 can be formed in arbitrary shapes by the electrically conductive fibers 300. As an example, heating elements 114 can be formed from single electrically conductive fibers 300. Alternatively, groups of electrically conductive fibers 300 can be placed in electrical communication with one another to form a single heating element that extends over a two-dimensional region of the woven pocket 106. Respective heating elements 114 can be separated from one another by one or more breaks 304 separating adjacent electrically conductive fibers 300. As an example, FIG. 3A illustrates two different heating elements 114a, 114b formed from two different groups of electrically conductive fibers 300 separated by a break 304.

The electrically conductive fibers 300 can be formed from any electrically conductive material. Examples of electrically conductive materials can include, but are not limited to, copper, copper alloys, aluminum, aluminum alloys, carbon, metal coated graphite, and combinations thereof. In certain embodiments, the electrically conductive fibers 300 can be formed from a positive temperature coefficient (PTC) material, which exhibits electrical resistivity that increases exponentially with increasing temperature. Beneficially, PTC materials are self-regulating and self-limiting, which can allow heating elements 114 constructed from PTC materials to maintain an approximately constant temperature and which can inhibit the heating elements 114 from exceeding a pre-determined temperature, without the need for regulating electronics or overheat protection.

The woven pocket 106 can also be configured to thermally insulate the mechanical vibrators 210 from heat generated by the heating elements 114. In particular, the electrically insulating fibers 302 can partially or fully surround the mechanical vibrators 210 for thermal insulation. The electrically insulating fibers 302 can be formed from materials including, but not limited to cotton and plastics.

The woven pocket 106 can also be configured to thermally insulate the temperature sensors 116 from heat generated by the heating elements 114. As shown in FIG. 3A, the temperature sensors 116 can be secured to the woven pocket 106 at positions spaced apart from at least a portion of the electrically conductive fibers 300 in order to prevent thermal damage to the temperature sensors 116. The temperature sensors 116 can also be mounted on and/or surrounded by thermally insulating barriers (not shown). The thermally insulating barriers can be formed, for example, from rubbers, silicones, and/or plastics. The thermally insulating barriers can reduce errors in temperature measurements acquired by the temperature sensors 116 due to heat generated by the electrically conductive fibers 300.

Figures 4A, 4B:
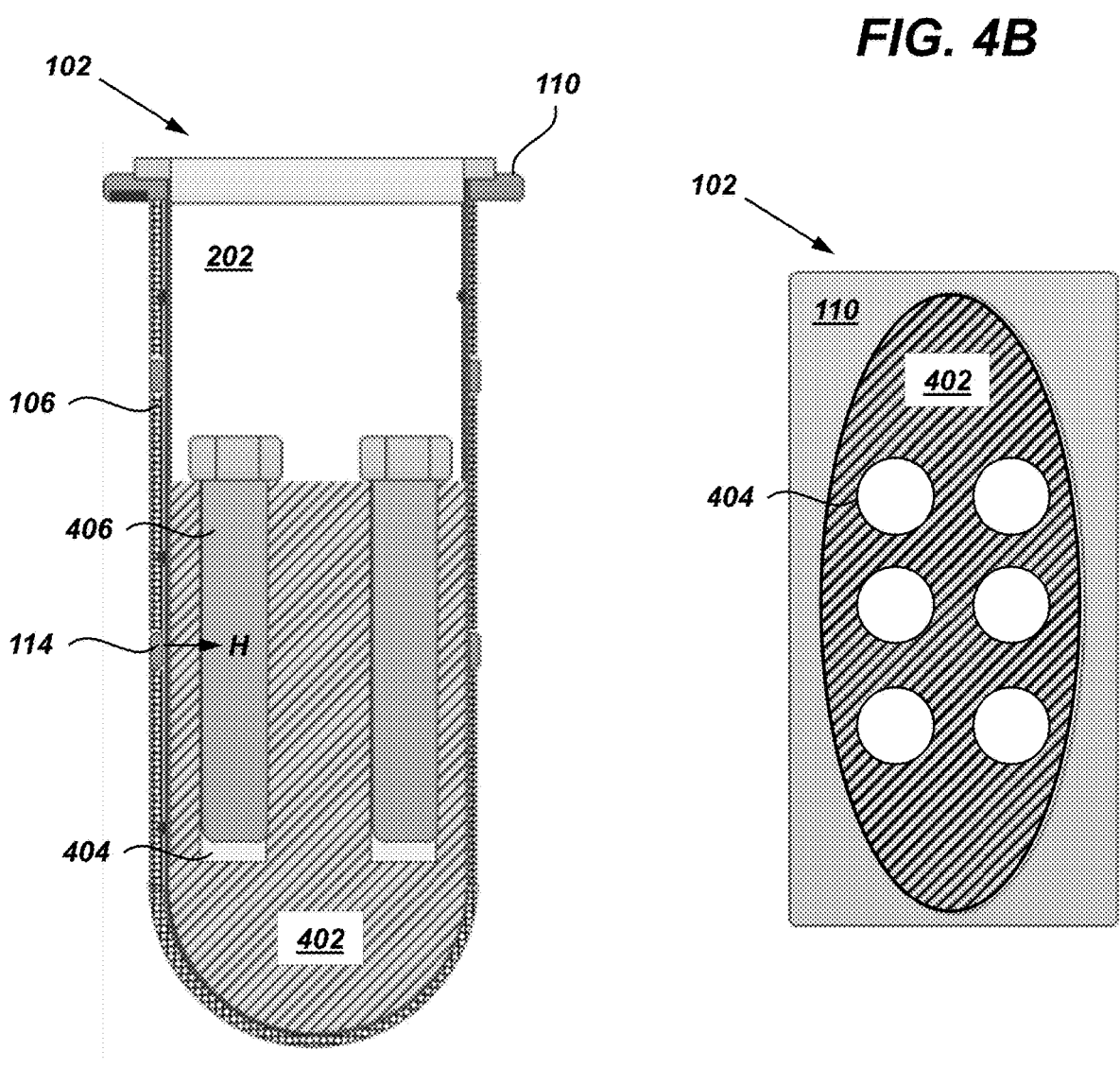
FIG. 4A is a side view of the dry thawing device of FIG. 2A including an adaptor.
FIG. 4B is a top view of the dry thawing device of FIG. 2A including the adaptor.

Embodiments of the dry thawing system 100 can also be configured to heat frozen biological samples contained within vessels other than the bag 112. As shown in FIGS. 4A-4B, the dry thawing system 100 can also include an adaptor 400 configured for use with the dry thawing device 102. The adaptor 400 can include a body 402 defining one or more chambers 404 each dimensioned to receive a vessel 406. The body 402 can also adopt a shape suitable for receipt within the inner volume 202 of the woven pocket 106 and contact with one or more of the heating elements 114. The body 402 can also be formed from a material having a relatively high thermal conductivity. Thus, a vessel 406 positioned within a chamber 404 of the adaptor 400 can receive heat H generated by the heating elements 114 and conducted through the body 202 for thawing a frozen biological substance contained therein. As shown in FIGS. 4A-4B, the vessels 406 are vials and the chambers 404 include six generally circular cylinders. However, the number and shape of the chambers can be varied to accommodate any number and shape of vessels as necessary.

Figure 5:
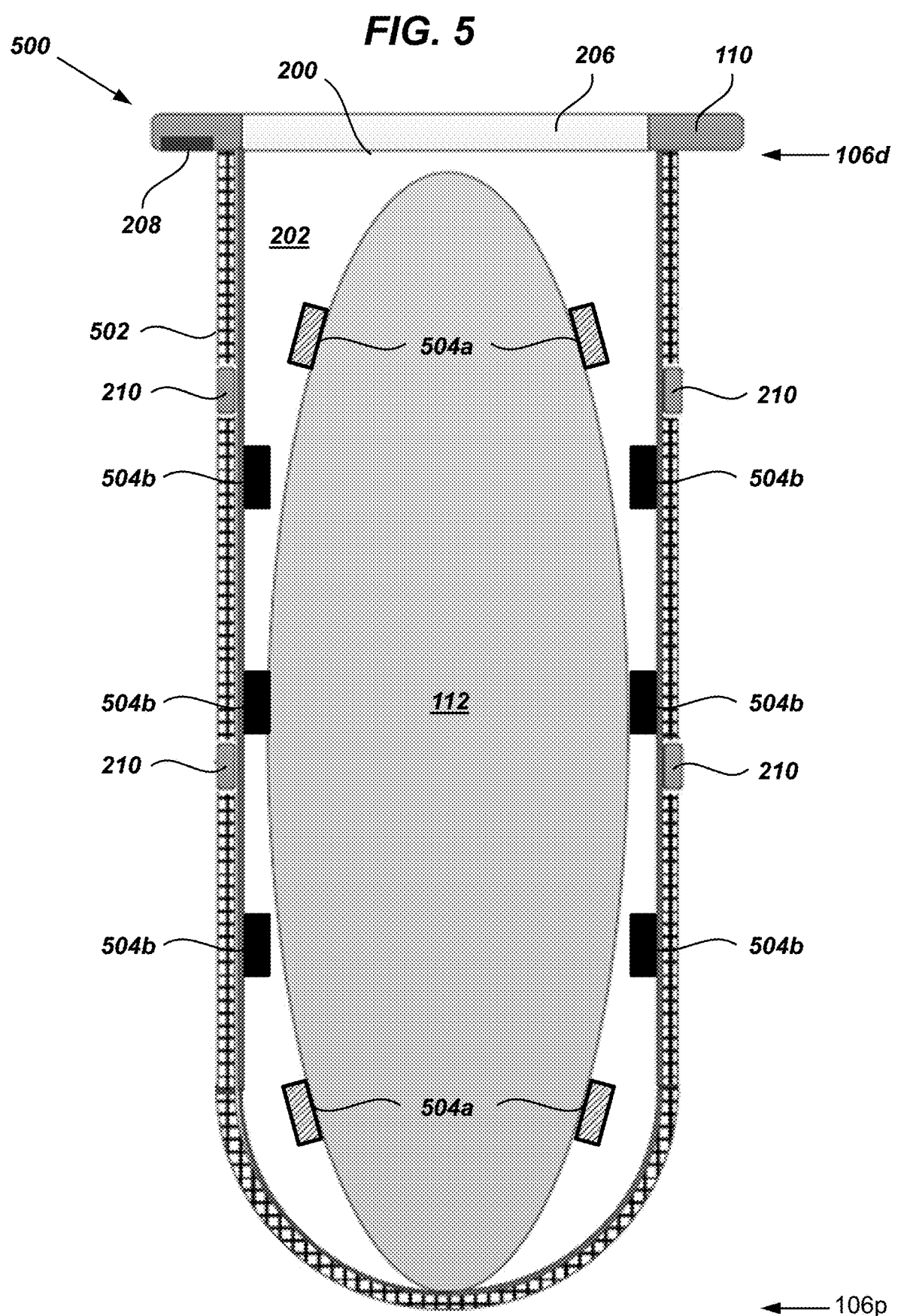
FIG. 5 is a side view of another exemplary embodiment of a dry thawing device.

FIG. 5 illustrates another embodiment of a dry thawing device 500. The dry thawing device 500 can be similar to the dry thawing device 102 except that the source of heat is different. As shown, the dry thawing device 500 can include a woven pocket 502 formed entirely from electrically insulating fibers. That is, the woven pocket 502 replaces the electrically conductive fibers 300 of the woven pocket 106 with electrically insulating fibers, such as electrically insulating fibers 302, discussed above.

The dry thawing device 500 can also include heating elements 504 (e.g., 504a, 504b) to supply heat to the inner volume 202. As shown in FIG. 5 the heating elements 504 can be positioned on an inner surface of the inner volume 202 of the woven pocket 502 (e.g., 504a) and/or be positioned on an outer surface of the bag 112 (e.g., 504b). As an example, multiple pairs of heating elements 504a and/or 504b can be spaced vertically from one another, with respective members of each pair positioned horizontally on opposite sides of the woven pocket 502.

The heating elements 504 can be formed as electrically conductive filaments (e.g., a positive temperature coefficient (PTC) material). Similar to the heating elements 114, the heating elements 504 can be provided in electrical communication with the electrical interface 208 of the frame 110 to receive commands from the computing device 104 for generating heat (e.g., resistive heating devices).

Figure 6:
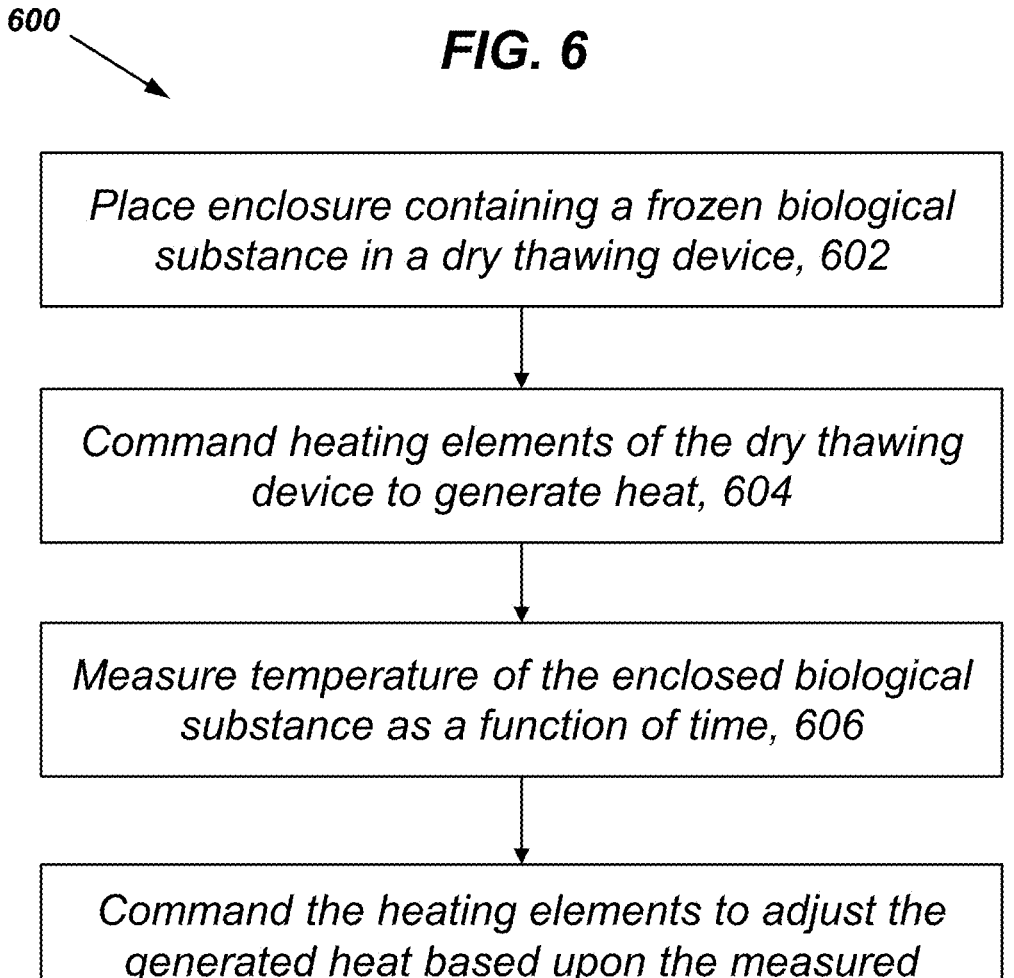
FIG. 6 is a diagram of an exemplary embodiment of a monitoring and control system for dry thawing biological substances.

One exemplary embodiment of a method 600 for thawing a biological sample is illustrated in FIG. 6. The method 600 can employ the dry thawing system 102 of FIG. 1 or the dry thawing device 500 of FIG. 5. The method 600 can include operations 602-610, described below. It may be understood that alternative embodiments of the method can add or omit one or more operations and the operations can be performed in a different order than illustrated in FIG. 6.

In operation 602, an enclosure containing a frozen biological substance (e.g., whole blood, blood products, plasma derivatives, etc.) such as the bag 112 can be received within the woven pocket 106, 502 of the dry thawing device 102, 500. The temperature sensors 116 and heating elements 114, 504 can be in thermal communication with the bag 112 (e.g., in direct contact) while the mechanical vibrators 210 can be in mechanical communication with the bag 112.

After the bag 112 containing a frozen biological substance is received within the woven pocket 106, 502, the dry thawing device 102, 500 can supply heat to the biological substances using the heating elements 114, 504 in operation 604. As an example, a user can actuate the dry thawing device 102, 500 causing a first signal to be provided to heating elements 114, 504 by the computing device 104 and can command the heating elements 114, 504 to generate heat.

In operation 606, the dry thawing device 102, 500 can measure the temperature of the bag 112. As an example, the temperature sensors 116 can each receive electrical power from the computing device 104 or another power source and, in response, output respective second signals representing temperature measurements of the outer surface of the bag 112 at the location of the temperature sensors 116. These temperature measurements can be made substantially continuously or at pre-defined time intervals. The computing device 104 can receive the second signals and, using calibrations for the temperature sensors 116, determine temperature measurements acquired by the temperature sensors 116 from the received second signals. The computing device 104 can also store temperature measurements acquired by each of the temperature sensors 116 as a function of time to provide a record of the temperature of the bag 112 during thawing.

Once the temperature of the bag 112 is measured by the temperature sensors 116, the computing device 104 can transmit a third command signal to the heating elements 114 in operation 610. The third command signal can be based upon one or more temperature measurements acquired by the temperature sensors 116 (e.g., an average of two or more temperature measurements). As an example, the third command signal can be based upon a temperature difference between the measured temperature of the bag 112 and a pre-defined temperature set point. If the measured temperature of the bag 112 is less than the temperature set point, the third command signal can command the heating elements 114 to generate heat. Conversely, if the measured temperature of the bag 112 is greater than the temperature set point, the third command signal can command the heating elements 114 to cease generation of heat. In this manner, the dry thawing process can be terminated as soon as the biological substance within the bag 112 reaches a desired temperature.

Before, during, or after generation of heat, the mechanical vibrators 210 can generate mechanical vibrations in order to agitate the biological contents. At the onset of the thawing process, heat can be transferred from the heating elements 114 to the biological substance by conduction through the bag 112. As the biological substance near the heated exterior of the bag 112 becomes liquefied, thermal convective flow can becomes more prominent. Thus, the low frequency mechanical vibrations provided by the mechanical vibrators 210 can inhibit concentration gradients from being formed during the thawing process and help to achieve an approximately homogeneous temperature profile within the bag 112. In certain embodiments, a 250 ml-500 ml bag containing a frozen biological substance can be thawed by the dry thawing device 102, 500 within approximately 10 minutes.

Embodiments of the disclosed dry thawing devices and methods can confer several advantages, as compared to conventional water baths and water bladders, when thawing bags of frozen biological substances. In one aspect, risk of microbial contamination can be reduced with elimination of contact between a water bath and a bag enclosing a biological substance. In another aspect, a biological substance can be thawed in an approximately uniform manner, reducing the risks of overheating, underthawing, and/or denaturation. In a further aspect, the disclosed systems and methods require relatively low maintenance compared to the disinfection and energy consumption required by conventional water baths and water bladders.

The above-described systems and methods can be implemented in digital electronic circuitry, in computer hardware, firmware, and/or software. The implementation can be as a computer program product. The implementation can, for example, be in a machine-readable storage device, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Subroutines and software agents can refer to portions of the computer program, the processor, the special circuitry, software, and/or hardware that implement that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network.

Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), IEEE 802.11 network, IEEE 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, Bluetooth®, code-division multiple access (CDMA) network, time division multiple access (TDMA) network, global system for mobile communications (GSM) network), and/or other circuit-based networks.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a World Wide Web browser (e.g., Microsoft® Internet Explorer® available from Microsoft Corporation, Mozilla® Firefox available from Mozilla Corporation, Chrome Browser available from Google®). The mobile computing device includes, for example, a Blackberry®.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

It must be noted that, as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

Whenever a range is given in the specification, for example, a temperature range, a time range, or a composition or concentration range, all intermediate ranges and sub-ranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any sub-ranges or individual values in a range or sub-range that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

A person skilled in the art will appreciate further features and advantages of the invention based on the above-described embodiments. Accordingly, the invention is not to be limited by what has been particularly shown and described, except as indicated by the appended claims. All publications and references cited herein are expressly incorporated by reference in their entirety.

What is claimed is:

1. A dry thawing device for dry thawing a biological substance, comprising:
  a frame comprising:
    an aperture, and
    a lip extending outward from the aperture, wherein the lip comprises an electrical interface;
  a flexible woven pocket having a woven distal end and an inner volume dimensioned to receive a container containing a biological substance, the flexible woven pocket comprising one or more electrically conductive fibers and one or more electrically insulating fibers interwoven together to form a woven side of the flexible woven pocket to flex according to a contour of the container,
    wherein the woven pocket is directly coupled to the frame and positioned within the aperture,
    wherein the woven pocket further comprises a temperature sensor disposed to be in the woven side in between the fibers of the woven side and configured to move along with the flexing woven side when the woven side flexes and to contact the container to thermally communicate with the biological substance received within the woven pocket;
  a heating element configured to supply heat to the inner volume of the woven pocket based upon a temperature measurement acquired by the temperature sensor;
  a mechanical vibrator configured to vibrate the flexible woven pocket and the biological substance contained in the container to facilitate homogenous thawing within the container.

2. The dry thawing device of claim 1, wherein the electrical interface is electrically coupled with the heating element and the temperature sensor.

3. The dry thawing device of claim 1, wherein the frame is a rigid frame.

4. The dry thawing device of claim 1, further comprising a liquid-resistant coating lining an inner surface of the woven pocket.

5. The dry thawing device of claim 1, further comprising an adaptor comprising a body defining a plurality of chambers, wherein the adaptor is positioned within the inner volume of the woven pocket and each chamber of the plurality of chambers is configured to receive a vessel containing a biological substance.

6. The dry thawing device of claim 5, wherein the body is thermally conductive.

7. The dry thawing device of claim 5, wherein each chamber of the plurality of chambers is cylindrical and configured to receive a vial.

8. A system for dry thawing a biological substance, comprising:
  the dry thawing device of claim 1, wherein the electrical interface is a first electrical interface; and
  a rigid housing dimensioned to enclose the dry thawing device therein and including a second electrical interface configured to engage the first electrical interface for delivering a command to the dry thawing device.

9. The system of claim 8, wherein the rigid housing is configured to support at least a portion of the dry thawing device at the frame.

10. The system of claim 8, wherein the heating element is configured to supply heat to the biological substance received within the woven pocket in response to the command.

11. The system of claim 10, wherein the heating element comprises an electrically conductive fiber integrated into the woven pocket.

12. The system of claim 8, wherein the temperature sensor is configured to communicate the acquired temperature measurement to the first electrical interface.

13. The system of claim 12, further comprising a computing device in communication with the second electrical interface, wherein the computing device is configured to receive the acquired temperature measurement and generate the command based upon a difference between the acquired temperature measurement and a pre-defined temperature set point.

14. The system of claim 8, wherein the mechanical vibrator is configured to generate the vibration at a frequency of from about 0.1 Hz to about 50 KHz, to agitate the biological substance in response to the command.

* * * * *